(12) United States Patent
Koshiol et al.

(10) Patent No.: US 11,855,292 B2
(45) Date of Patent: Dec. 26, 2023

(54) BUSBAR CONNECTION FOR MULTIPLATE BATTERY

(71) Applicant: Cardiac Pacemakers, Inc., St. Paul, MN (US)

(72) Inventors: Kurt E. Koshiol, Minnetonka, MN (US); Ignacio Chi, Mahtomedi, MN (US); Joseph Charles Delmedico, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 16/850,642

(22) Filed: Apr. 16, 2020

(65) Prior Publication Data

US 2020/0335747 A1 Oct. 22, 2020

Related U.S. Application Data

(60) Provisional application No. 62/835,149, filed on Apr. 17, 2019.

(51) Int. Cl.

| *H01M 4/70* | (2006.01) |
|---|---|
| *H01M 50/516* | (2021.01) |
| *H01M 50/209* | (2021.01) |
| *H01M 50/54* | (2021.01) |
| *H01M 50/507* | (2021.01) |
| *H01M 50/103* | (2021.01) |
| *H01M 50/55* | (2021.01) |

(Continued)

(52) U.S. Cl.
CPC ........... *H01M 4/70* (2013.01); *H01M 50/103* (2021.01); *H01M 50/209* (2021.01); *H01M 50/507* (2021.01); *H01M 50/516* (2021.01); *H01M 50/54* (2021.01); *H01M 50/55* (2021.01); *H01M 50/553* (2021.01); *A61N 1/3706* (2013.01)

(58) Field of Classification Search
CPC .. H01M 50/20; H01M 50/502; H01M 50/543; H01M 50/54; H01M 50/10; H01M 4/70; A61N 1/3706
See application file for complete search history.

(56) References Cited

U.S. PATENT DOCUMENTS

| 6,040,082 A | 3/2000 | Haas et al. |
|---|---|---|
| 6,185,452 B1 | 2/2001 | Schulman et al. |

(Continued)

*Primary Examiner* — Brian R Ohara
*Assistant Examiner* — Emily Elizabeth Freeman
(74) *Attorney, Agent, or Firm* — Pauly, DeVries Smith & Deffner LLC

(57) ABSTRACT

Embodiments herein relate to simplified and space efficient designs for multiplate batteries. In an embodiment, an electrochemical cell is included having an multiplate anode and multiplate cathode with a separator to provide physical separation between anode and cathode plates. Anode collectors can be in electrical communication with each anode plate and anode tabs in electrical communication with each anode collector. Cathode collectors can be in electrical communication with each cathode plate and cathode tabs in electrical communication with each cathode collector. An anode busbar can interconnect the plurality of anode tabs in parallel and a cathode busbar can interconnect the plurality of cathode tabs in parallel. The cathode busbar can be oriented such that the cathode tabs are not disposed between the cathode busbar and the plurality of cathode plates. Other embodiments are also included herein.

15 Claims, 13 Drawing Sheets

(51) Int. Cl.
*H01M 50/553* (2021.01)
*A61N 1/37* (2006.01)

(56) References Cited

U.S. PATENT DOCUMENTS

| | | |
|---|---|---|
| 7,858,236 B2 | 12/2010 | Howard et al. |
| 8,916,290 B2 | 12/2014 | Aamodt et al. |
| 10,205,204 B2 | 2/2019 | Kong et al. |
| 10,637,018 B2 | 4/2020 | Inakawa et al. |
| 2004/0048149 A1* | 3/2004 | Gross ............... H01M 50/184 |
| | | 429/185 |
| 2008/0221629 A1 | 9/2008 | Morgan et al. |
| 2011/0123857 A1* | 5/2011 | Hwang ............... H01M 50/531 |
| | | 429/185 |
| 2012/0107670 A1* | 5/2012 | Viavattine ......... H01M 10/0436 |
| | | 429/153 |
| 2013/0323542 A1* | 12/2013 | Wijayawardhana .. H01M 10/48 |
| | | 324/426 |
| 2016/0013455 A1* | 1/2016 | Shiu .................... H01M 50/557 |
| | | 156/227 |
| 2017/0317331 A1 | 11/2017 | Vedoy |

\* cited by examiner

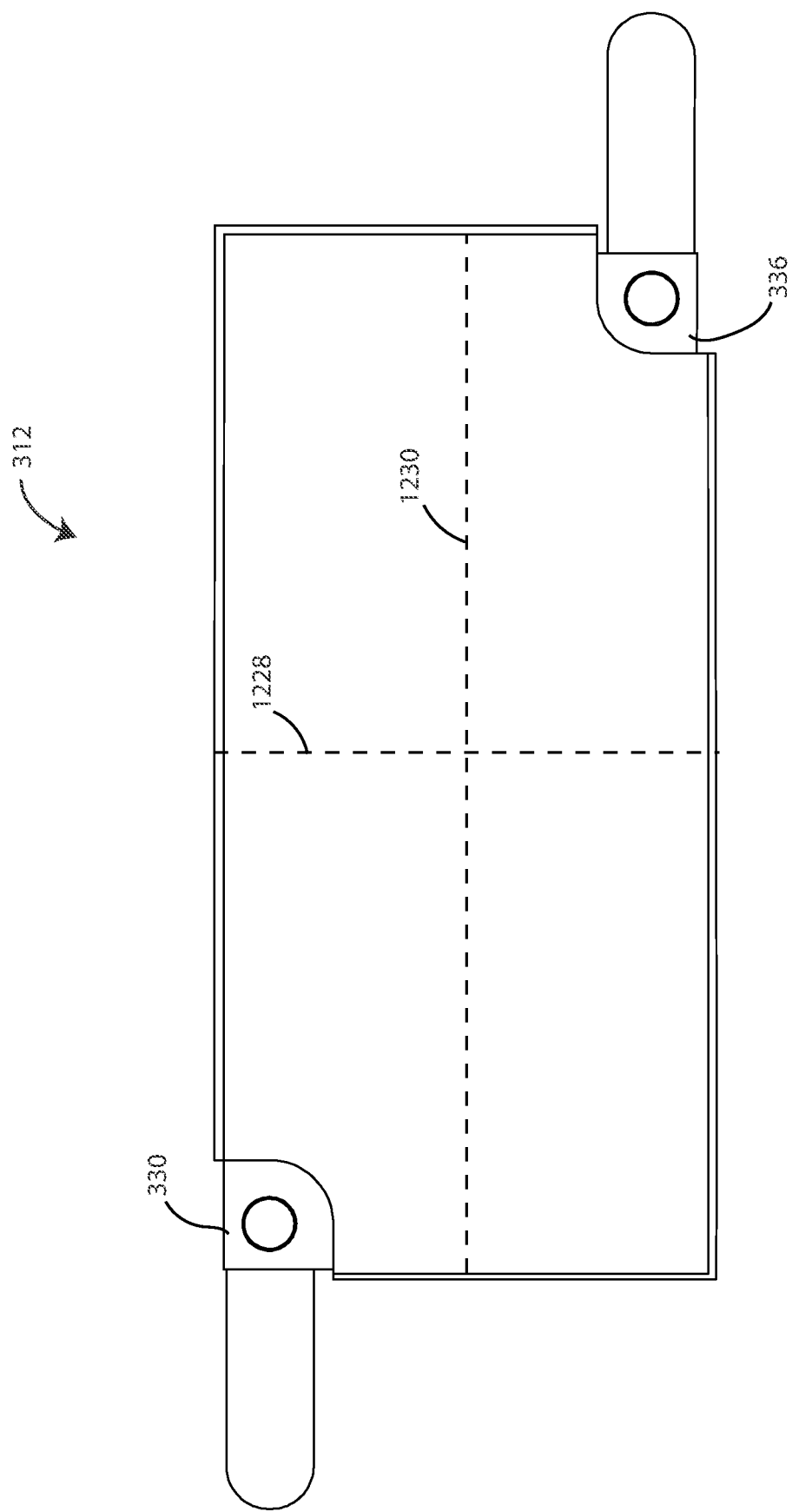

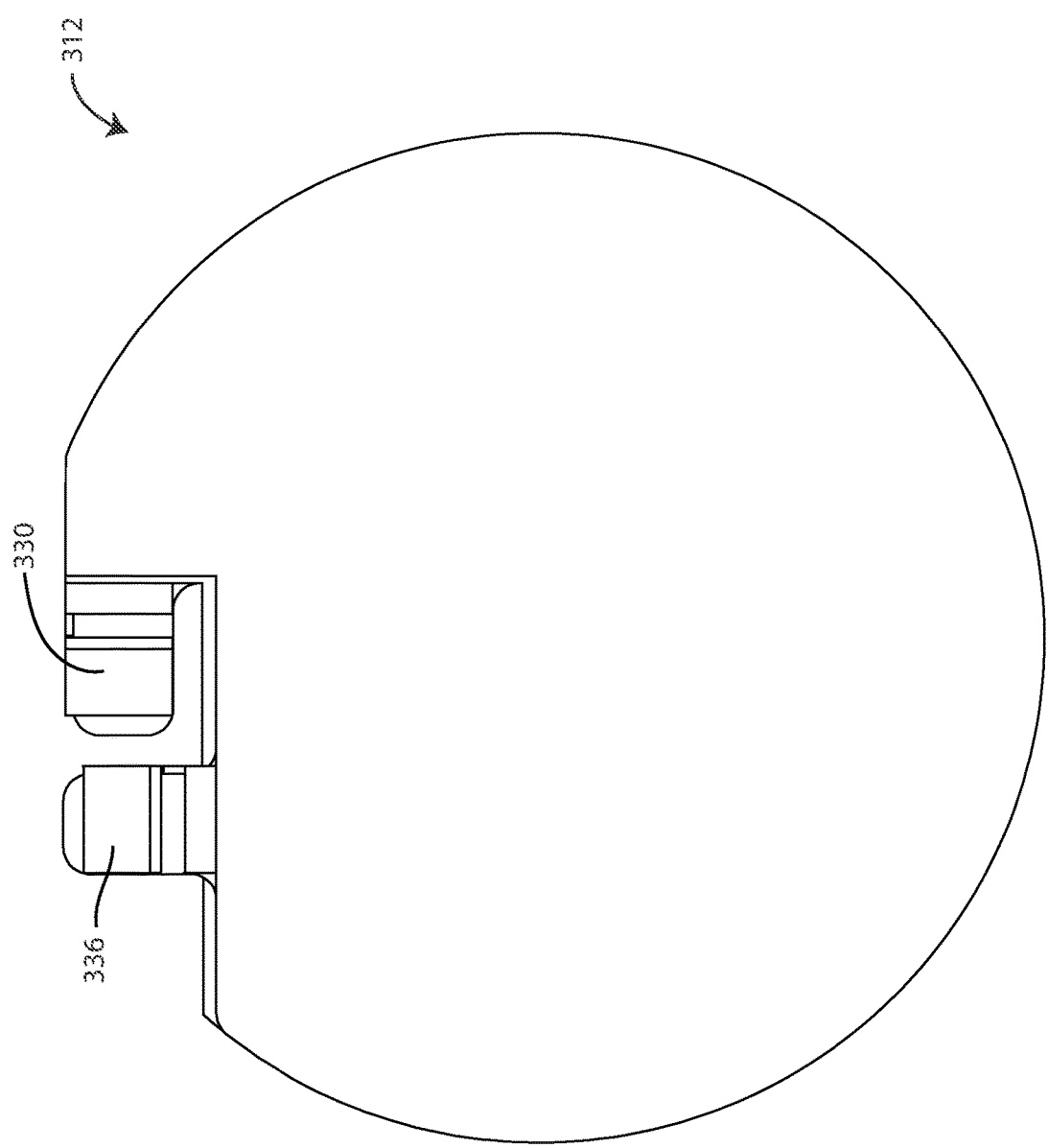

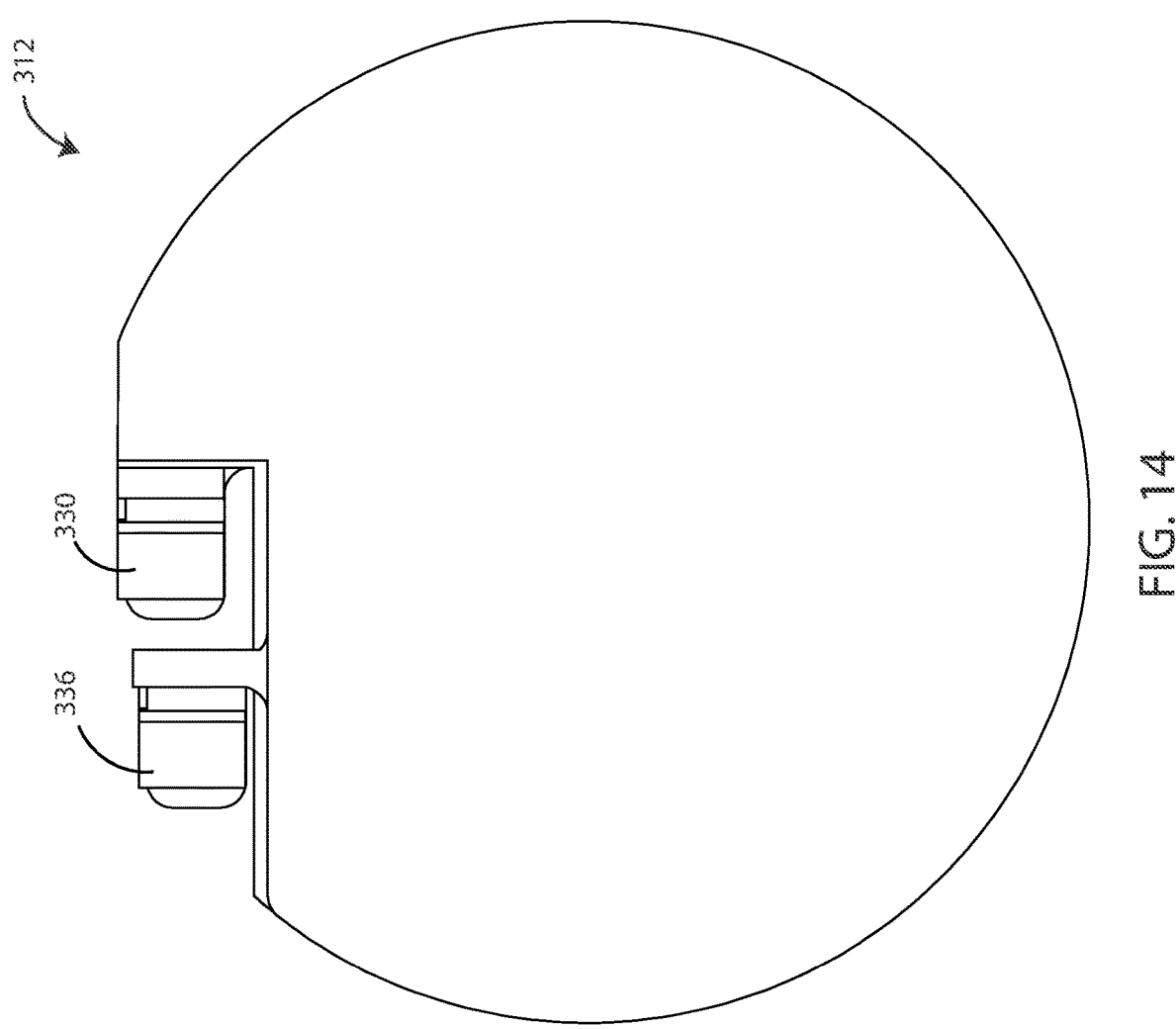

BUSBAR CONNECTION FOR MULTIPLATE BATTERY

This application claims the benefit of U.S. Provisional Application No. 62/835,149 filed Apr. 17, 2019, the content of which is herein incorporated by reference in its entirety.

FIELD

Embodiments herein relate to simplified and space efficient designs for multiplate batteries.

BACKGROUND

Implantable medical devices are now commonly used for monitoring a patient's condition and in some cases also administering therapy to the patient. In some cases, the implantable medical device may be implanted only temporarily. In other cases, the implantable medical device may be implanted chronically over a period of years.

Some types of implantable medical device include electronic circuitry to provide various monitoring or therapeutic functions. Therefore, such devices require electrical power, which is frequently provided by a battery.

The overall size of the implanted device is relevant because reduced device size can boost patient comfort as well as allow for greater placement site and placement method flexibility.

SUMMARY

Embodiments herein relate to simplified and space efficient designs for multiplate batteries. In a first aspect, an electrochemical cell is included having an anode including a plurality of anode plates and a cathode including a plurality of cathode plates. The cathode plates can be interposed between adjacent anode plates forming a stack of alternating anode and cathode plates. A separator can be positioned to provide physical separation between anode and cathode plates. A plurality of anode collectors can be in electrical communication with each anode plate. A plurality of anode tabs can be in electrical communication with each anode collector. A plurality of cathode collectors can be in electrical communication with each cathode plate. A plurality of cathode tabs can be in electrical communication with each cathode collector. An anode busbar can interconnect the plurality of anode tabs in parallel. A cathode busbar can interconnect the plurality of cathode tabs in parallel. The cathode busbar can be oriented substantially perpendicularly to a plane of the anode and cathode plates. The cathode busbar can be oriented such that the cathode tabs are not disposed between the cathode busbar and the plurality of cathode plates.

In a second aspect, in addition to one or more of the preceding or following aspects, or in the alternative to some aspects, the anode busbar can be oriented substantially perpendicularly to a plane of the anode and cathode plates, wherein the anode busbar is oriented such that the anode tabs are not disposed between the anode busbar and the plurality of anode plates.

In a third aspect, in addition to one or more of the preceding or following aspects, or in the alternative to some aspects, the anode busbar can be welded to the plurality of anode plates and the cathode busbar can be welded to the plurality of cathode plates.

In a fourth aspect, an electrochemical cell is included having an anode that can include a plurality of anode plates and a cathode that can include a plurality of cathode plates. The cathode plates can be interposed between adjacent anode plates forming a stack of alternating anode and cathode plates. A separator can be positioned to provide physical separation between anode and cathode plates. A plurality of anode collectors can be in electrical communication with each anode plate. A plurality of anode tabs can be in electrical communication with each anode collector. A plurality of cathode collectors can be in electrical communication with each cathode plate. A plurality of cathode tabs can be in electrical communication with each cathode collector. An anode busbar can interconnect the plurality of anode tabs in parallel. A cathode busbar can interconnect the plurality of cathode tabs in parallel. The cathode tabs can extend a first distance outward from an adjacent edge of the cathode plates. The cathode busbar can be positioned at a second distance outward from the adjacent edge of the cathode plates. The second distance can be less than or equal to the first distance.

In a fifth aspect, in addition to one or more of the preceding or following aspects, or in the alternative to some aspects, the anode tabs can extend a third distance outward from an adjacent edge of the anode plates, wherein the anode busbar is positioned at a fourth distance outward from the adjacent edge of the anode plates, and wherein the fourth distance is less than or equal to the third distance.

In a sixth aspect, an electrochemical cell is included having an anode that can include a plurality of anode plates and a cathode that can include a plurality of cathode plates. The cathode plates can be interposed between adjacent anode plates forming a stack of alternating anode and cathode plates. A separator can be positioned to provide physical separation between anode and cathode plates. A plurality of anode collectors can be in electrical communication with each anode plate. A plurality of anode tabs can be in electrical communication with each anode collector. A plurality of cathode collectors can be in electrical communication with each cathode plate. A plurality of cathode tabs can be in electrical communication with each cathode collector. An anode busbar can interconnect the plurality of anode tabs in parallel. A cathode busbar can interconnect the plurality of cathode tabs in parallel. The cathode tabs can include an outside edge. The cathode busbar can include an outside edge. The outside edge of the cathode tabs can be farther away from a centerline of the cathode plates than the outside edge of the cathode busbar.

In a seventh aspect, in addition to one or more of the preceding or following aspects, or in the alternative to some aspects, the anode tabs can include an outside edge, the anode busbar can include an outside edge, and the outside edge of the anode tabs can be farther away from a centerline of the anode plates than the outside edge of the anode busbar.

In an eighth aspect, an electrochemical cell is included having an anode including a plurality of anode plates each having outside peripheral surfaces and a cathode including a plurality of cathode plates each having outside peripheral surfaces. The cathode plates can be interposed between adjacent anode plates forming a stack of alternating anode and cathode plates. A separator can be positioned to provide physical separation between anode and cathode plates. A plurality of anode collectors can be in electrical communication with each anode plate. A plurality of anode tabs can be in electrical communication with each anode collector. A plurality of cathode collectors can be in electrical communication with each cathode plate. A plurality of cathode tabs can be in electrical communication with each cathode collector. An anode busbar can interconnect the plurality of anode tabs in parallel. A cathode busbar can interconnect the plurality of cathode tabs in parallel. The outside peripheral surfaces of the cathode plates can define a first perimeter. The cathode plates can define a first void falling within the first perimeter. The cathode busbar can be disposed within the first perimeter.

In a ninth aspect, in addition to one or more of the preceding or following aspects, or in the alternative to some aspects, the outside peripheral surfaces of the anode plates can define a second perimeter, the anode plates can define a second void falling within the second perimeter, and the anode busbar can be disposed within the second perimeter.

In a tenth aspect, in addition to one or more of the preceding or following aspects, or in the alternative to some aspects, the first void can be positioned adjacent to a corner of the cathode plates.

In an eleventh aspect, in addition to one or more of the preceding or following aspects, or in the alternative to some aspects, the first void can include less than 10 percent of the total surface area of the cathode plates.

In a twelfth aspect, in addition to one or more of the preceding or following aspects, or in the alternative to some aspects, the second void can be positioned to be adjacent a corner of the anode plates.

In a thirteenth aspect, in addition to one or more of the preceding or following aspects, or in the alternative to some aspects, the second void can include less than 10 percent of the total surface area of the anode plates.

In a fourteenth aspect, in addition to one or more of the preceding or following aspects, or in the alternative to some aspects, the anode tabs can define an aperture into which the anode busbar fits.

In a fifteenth aspect, in addition to one or more of the preceding or following aspects, or in the alternative to some aspects, the cathode tabs can define an aperture into which the cathode busbar fits.

In a sixteenth aspect, in addition to one or more of the preceding or following aspects, or in the alternative to some aspects, the cathode plates and the anode plates can be substantially rectangular.

In a seventeenth aspect, in addition to one or more of the preceding or following aspects, or in the alternative to some aspects, two corners can include a convex curve and two corners can include a concave curve.

In an eighteenth aspect, in addition to one or more of the preceding or following aspects, or in the alternative to some aspects, the cathode plates and the anode plates can be substantially circular.

In a nineteenth aspect, in addition to one or more of the preceding or following aspects, or in the alternative to some aspects, the first void can cover a surface area of 0.1 to 100 $mm^2$.

In a twentieth aspect, in addition to one or more of the preceding or following aspects, or in the alternative to some aspects, the second void can cover a surface area of 0.1 to 100 $mm^2$.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 12 is a top view of an electrochemical cell in accordance with various embodiments herein.

FIG. 13 is a top view of an electrochemical cell in accordance with various embodiments herein.

FIG. 14 is a top view of an electrochemical cell in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

In many cases, implantable medical devices are powered and contain a battery to provide such power. While there is a general trend across many implanted medical devices towards reduced size, the demand for power has remained constant or increased in some cases.

Batteries can consume a significant amount of space within an implanted device that is designed to be implanted over extended periods of time. After the active components of a battery such as the anode and cathode materials, it has been found that the most significant volume of space in a battery is used to form interconnects from the stack of alternating anode and cathode plates to the terminals. The volume of space required for the interconnects can be even larger in multiplate, stacked, designs due to geometries required to line up all of the components in the proper orientations to complete the interconnects.

Various embodiments disclosed herein utilize a space efficient busbar construction for the collection and distribution of current between the electrode plates and the battery terminals. In some embodiments, the busbar can be disposed directly adjacent to the anode and cathode plates, or within a profile, or recess, edge indentation, or edge cavity of the anode or cathode plates. When positioned as such, active materials can occupy the space in the battery otherwise left unutilized. Therefore, in accordance with embodiments herein, the amount of the total volume occupied by active materials can be maximized leading to a higher capacity battery per unit volume compared to an otherwise identical battery with a different and less space-efficient busbar placement.

The configurations of batteries herein including a busbar can reduce or eliminate the need for pinching layers together to prepare for welding and as a result can reduce the risk for short circuits between layers. Various embodiments disclosed herein also require fewer components and welding operations, as well as provide additional layer alignment. Various embodiments disclosed herein can enable a more compact design increasing energy density when considering the total space dedicated to the battery and can provide a more volumetrically efficient medical device.

Figure 1:
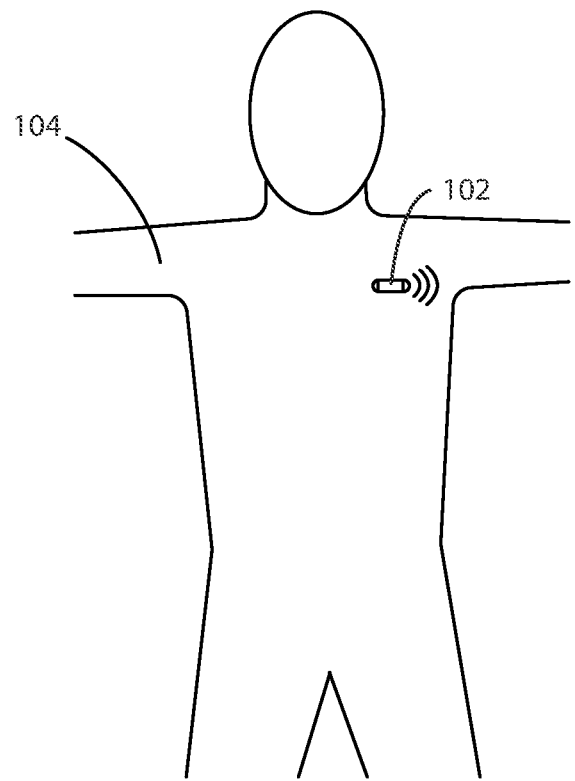
FIG. 1 is a schematic view of an implantable medical device implanted within a patient in accordance with various embodiments herein.

Referring now to FIG. 1, a schematic view is shown of an implantable medical device 102 with a space-efficient battery implanted within a patient 104 in accordance with various embodiments herein. In various embodiments, at least a portion of the medical device system can be implantable. In some embodiments, the implantable medical device 102 can include an implantable loop recorder, an implantable monitor device (such as an implantable cardiac monitor), a pacemaker, an implantable cardioverter-defibrillator, a neurostimulator device, or other electrical stimulation device, or the like. In some embodiments, the entire implantable medical device 102 can be implanted within the body of a patient 104. Various implant sites can be used including areas on the limbs, the upper torso, the abdominal area, and the like. In some embodiments, the implantable medical device 102 can be implanted subcutaneously. In some embodiments, a medical device system herein can include one or more additional medical devices that are communicatively coupled to one another.

Figure 2:
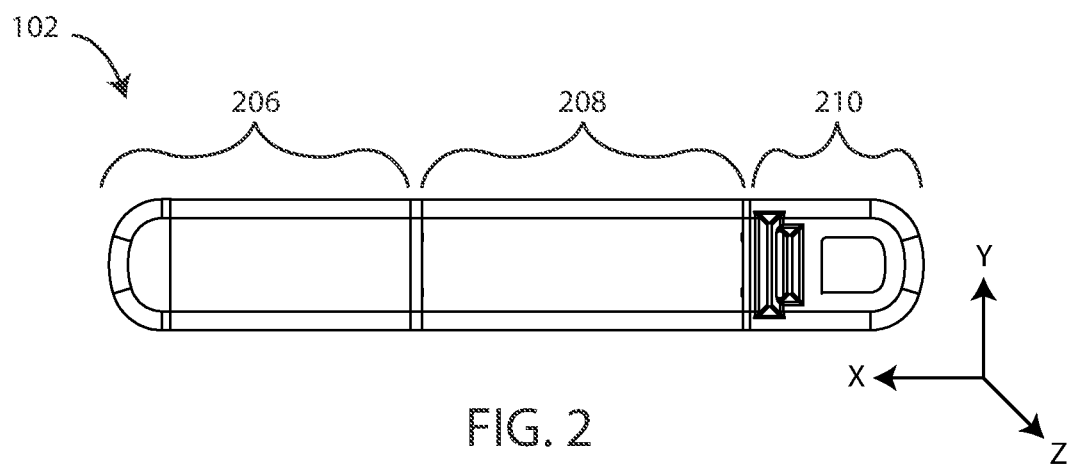
FIG. 2 is a schematic view of an implantable medical device in accordance with various embodiments herein.

It will be appreciated that many different types of implantable medical devices may be equipped with battery constructions as described herein. However, referring now to FIG. 2, a schematic view is shown of one exemplary type of an implantable medical device 102 in accordance with various embodiments herein. In some embodiments, the implantable medical device 102 can include a power subunit 206, an electronics control subunit 208, and a wireless communications subunit 210. The power subunit 206 can include components of an electrochemical cell, such as a multiplate battery described herein. The electronics control subunit 208 can include electronic components to control operations of the device including, for example, a controller or control circuit.

The power subunit 206 can be coupled to the electronics control subunit 208. In some embodiments, the power subunit 206 can be welded to the electronics control subunit 208. Welding can be performed using various techniques including laser welding. Exemplary welding techniques are described in greater detail below.

The implantable medical device 102 can have various dimensions, but in various cases is not particularly limited. However, in some embodiments the overall length (X axis) can be greater than or equal to 1, 3, 5, 7, 9, 10, 12, 14, 16, 18, or 20 mm. In some embodiments, the length can be less than or equal to 100, 80, 74, 68, 62, 56, 50, 44, 38, 32, 26, or 20 mm. In some embodiments, the length can fall within a range of 1 to 80 mm, or 3 to 74 mm, or 5 to 68 mm, or 7 to 62 mm, or 9 to 56 mm, or 10 to 50 mm, or 12 to 44 mm, or 14 to 38 mm, or 16 to 32 mm.

The overall width (Y axis) can be greater than or equal to 1, 5, 10, 15, 20, or 25 mm. In some embodiments, the width can be less than or equal to 50, 40, 30, 20, 15, or 10 mm. In some embodiments, the width can fall within a range between any of the foregoing.

The overall depth (Z axis) can be greater than or equal to 1, 5, 10, 15, 20, or 25 mm. In some embodiments, the depth can be less than or equal to 30, 20, 15, 10, or 5 mm. In some embodiments, the depth can fall within a range between any of the foregoing.

System Components

Figure 3:
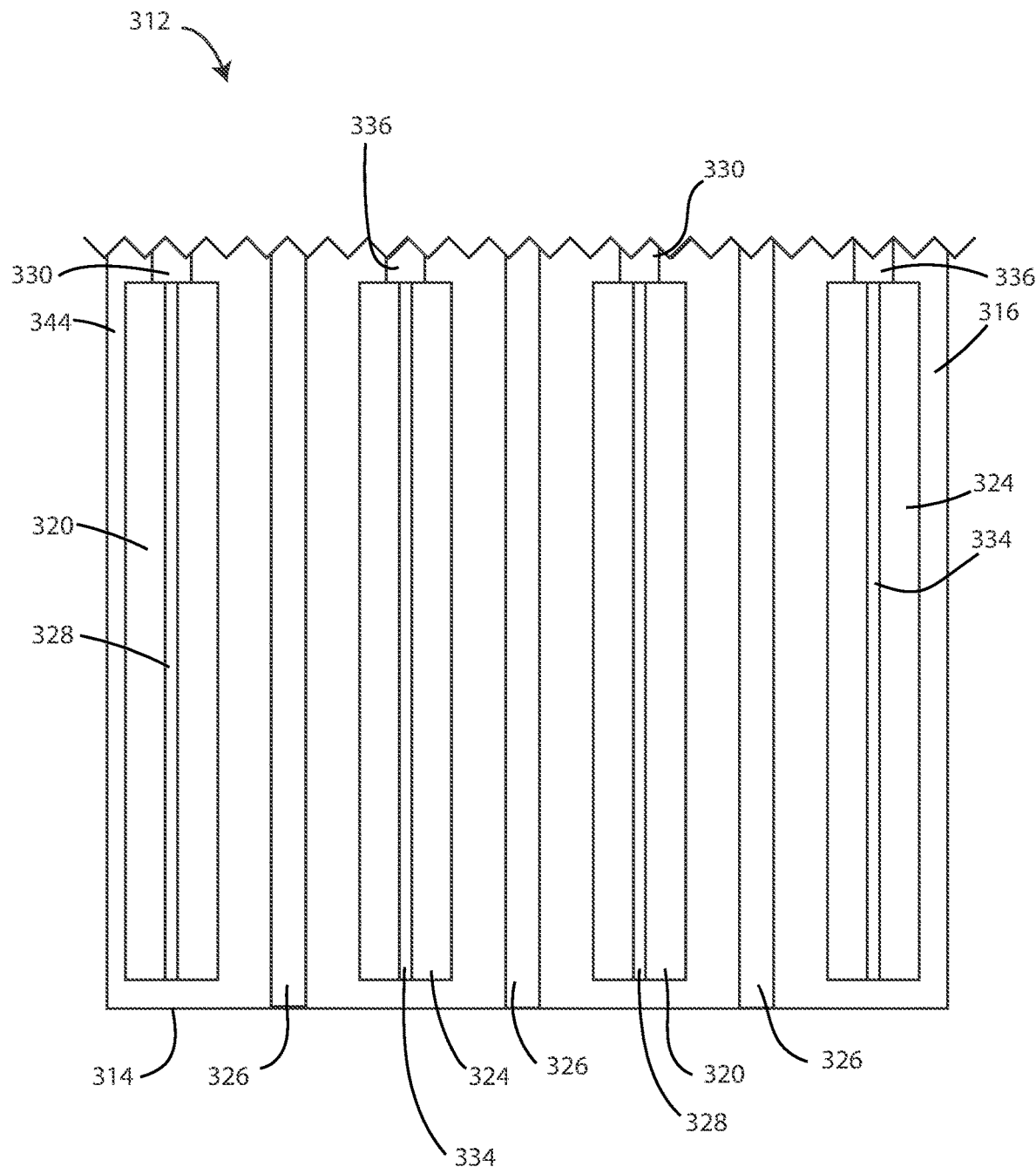
FIG. 3 is a schematic view of an electrochemical cell in accordance with various embodiments herein.

It will be appreciated that electrochemical cells or batteries can include various components. In reference now to FIG. 3, a schematic view of some components of an electrochemical cell 312 is shown in accordance with various embodiments herein. The electrochemical cell 312 (in some instances referred to as a multiplate battery) can include a housing 314 defining an interior volume 316.

Figure 5:
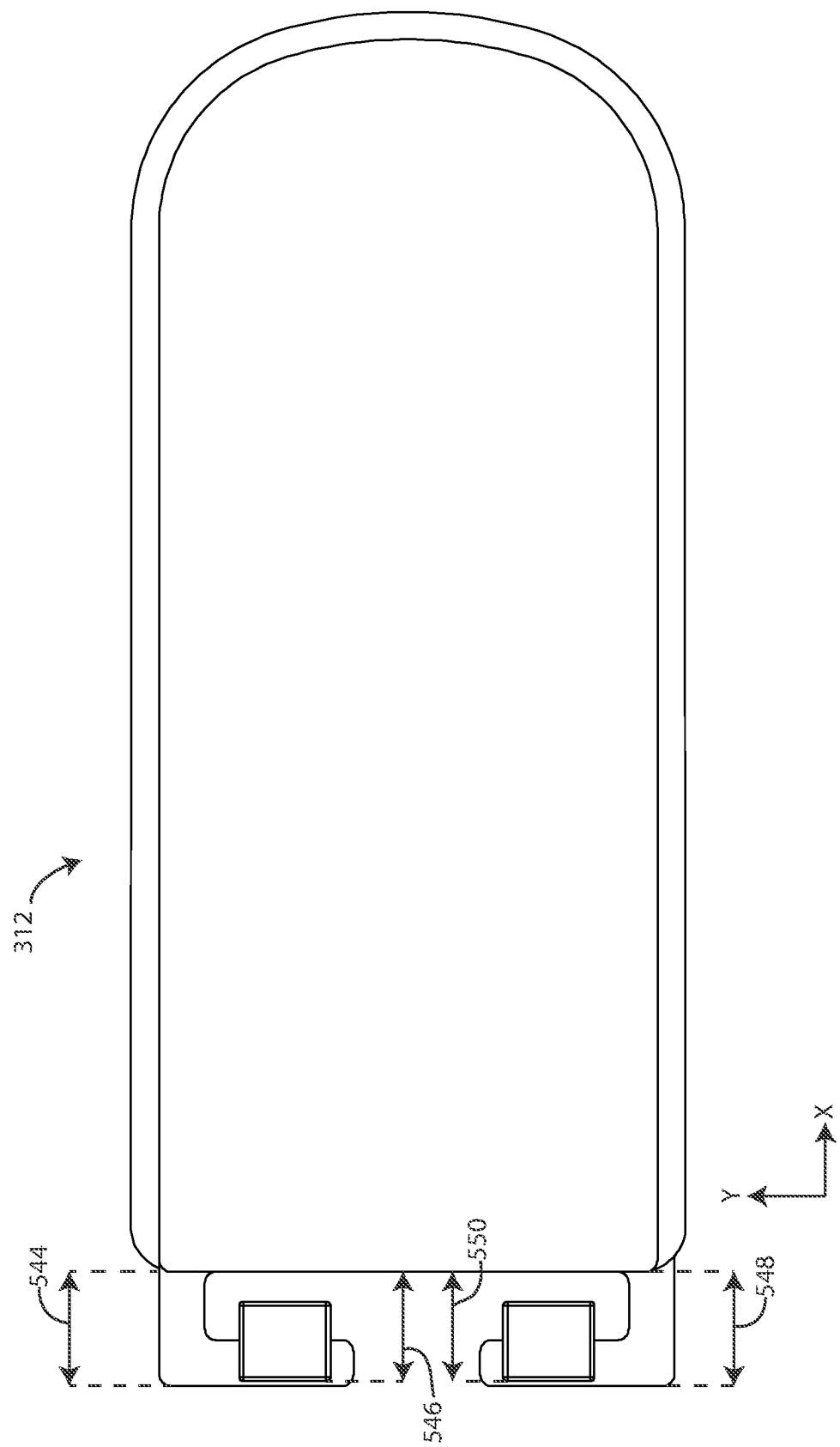
FIG. 5 is a top view of an electrochemical cell in accordance with various embodiments herein.

The electrochemical cell 312 can include an anode including a plurality of anode plates 320, and a cathode including a plurality of cathode plates 324. In some embodiments, the cathode plates 324 can be interposed between adjacent anode plates 320, such as to form a stack of alternating anode plates 320 and cathode plates 324. In some embodiments, the anode plates 320 and the cathode plates 324 can be substantially rectangular. In some embodiments, the anode plates 320 and/or the cathode plate 324, may define one or more voids, recesses, edge indentations, or edge cavities (not shown in this view). In some embodiments, the anode plates 320 and the cathode plates 324 can be circular or rounded. In some embodiments, the anode plates 320 and the cathode plates 324 can include at least one axis of symmetry, such as shown in FIG. 5. In some embodiments, the anode plates 320 and the cathode plates 324 include one axis of symmetry, but not two axes of symmetry. In some embodiments, the anode plates 320 and the cathode plates 324 do not include an axis of symmetry, such as shown in FIG. 12.

In various embodiments, the electrochemical cell 312 can further include one or more separators 326. The separator 326 can be positioned to provide physical separation between each of the anode plates 320 and each of the cathode plates 324, such as to prevent shorting between the plates 320, 324.

In various embodiments, the electrochemical cell 312 can further include a plurality of anode collectors 328 and a plurality of anode tabs 330. In some embodiments, the anode collectors 328 and anode tabs 330 may be integral with one another. In some embodiments, the anode collectors 328 and anode tabs 330 can be welded, soldered, brazed, crimped, staked, or otherwise connected with one another so that they are in electrical communication with one another. In some embodiments, the anode collectors 328 and anode tabs 330 can be formed of the same conductive material (such as a metal) and in other embodiments they can be formed of different materials.

The anode collectors 328 can be in electrical communication with each anode plate 320, such as one anode collector 328 for each anode plate 320. The plurality of anode tabs 330 can be in electrical communication with each of the anode collectors 328, such as one anode tab 330 for each anode collector 328. An anode busbar (not shown in this view) can interconnect the anode tabs 330 in parallel.

In various embodiments, the electrochemical cell 312 can further include a plurality of cathode collectors 334 and a plurality of cathode tabs 336. In some embodiments, the cathode collectors 334 and cathode tabs 336 may be integral with one another. In some embodiments, the cathode collectors 334 and cathode tabs 336 can be welded, soldered, brazed, or otherwise connected with one another so that they are in electrical communication with one another. In some embodiments, the cathode collectors 334 and cathode tabs 336 can be formed of the same conductive material (such as a metal) and in other embodiments they can be formed of different materials.

The cathode collectors 334 can be in electrical communication with each cathode plate 324, such as one cathode collector 334 for each cathode plate 324. The plurality of cathode tabs 336 can be in electrical communication with each of the cathode collectors 334, such as one cathode tab 336 for each cathode collector 334. A cathode busbar (not shown in this view) can interconnect the cathode tabs 336 in parallel.

In some embodiments, the anode busbar 432 can be welded to the plurality of anode plates 320, such as at the anode tabs 330. In some embodiments, the cathode busbar 438 can be welded to the plurality of cathode plates 324, such as at the cathode tabs 336.

In some embodiments, the plates 320, 324, the collectors 328, 334, the tabs 330, 336, and the busbars can be disposed within the interior volume 316. In various embodiments, an anode terminal and a cathode terminal can be connected to the busbars and can be partially disposed within the interior volume 316, partially disposed outside of the interior volume 316, or fully disposed outside of the interior volume 316. Further, the interior volume 316 can be at least partially filled with an electrolyte material 344 or solution.

Busbar and Tab Arrangements

Figure 4:
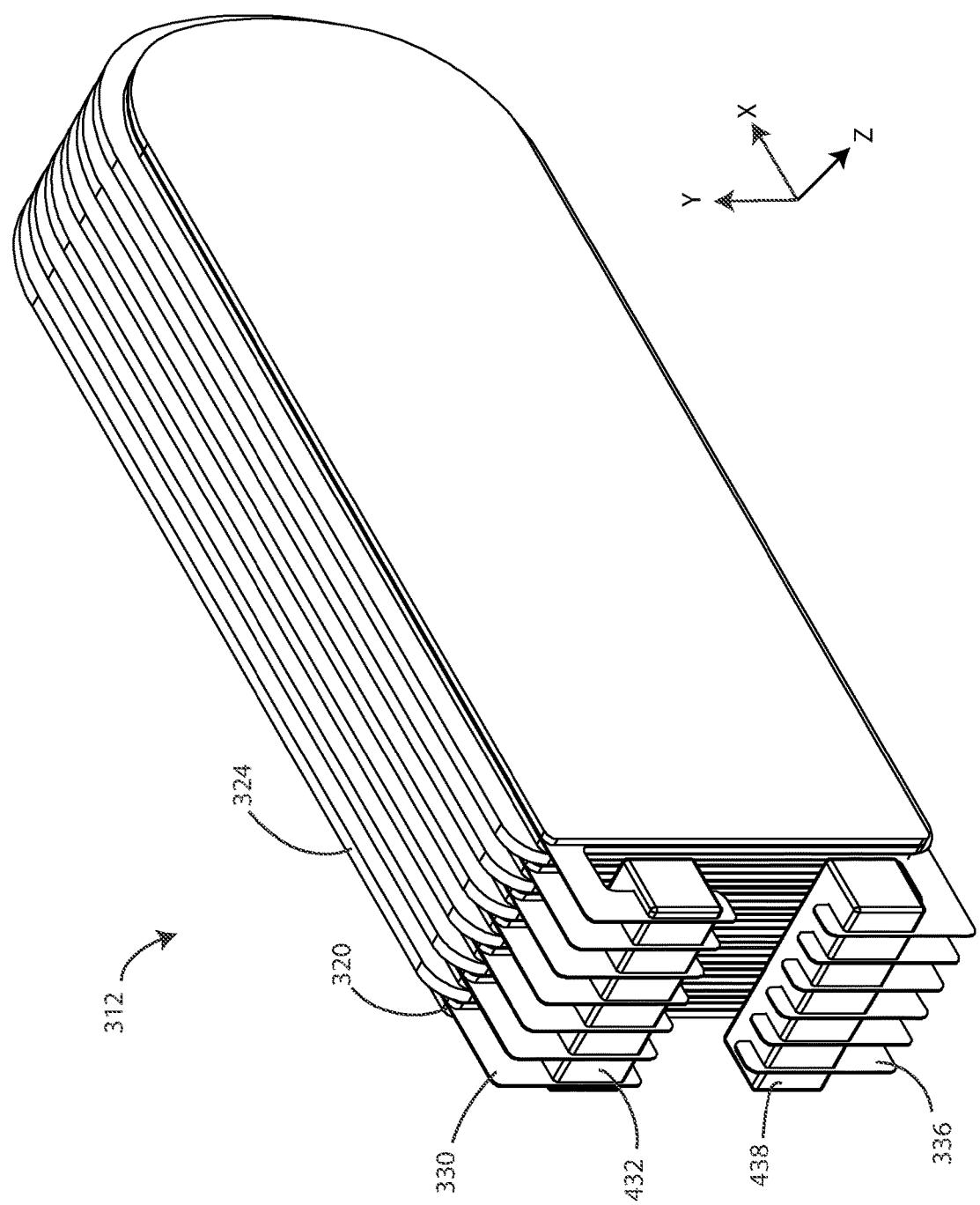
FIG. 4 is a perspective view of an electrochemical cell in accordance with various embodiments herein.
Figure 6:
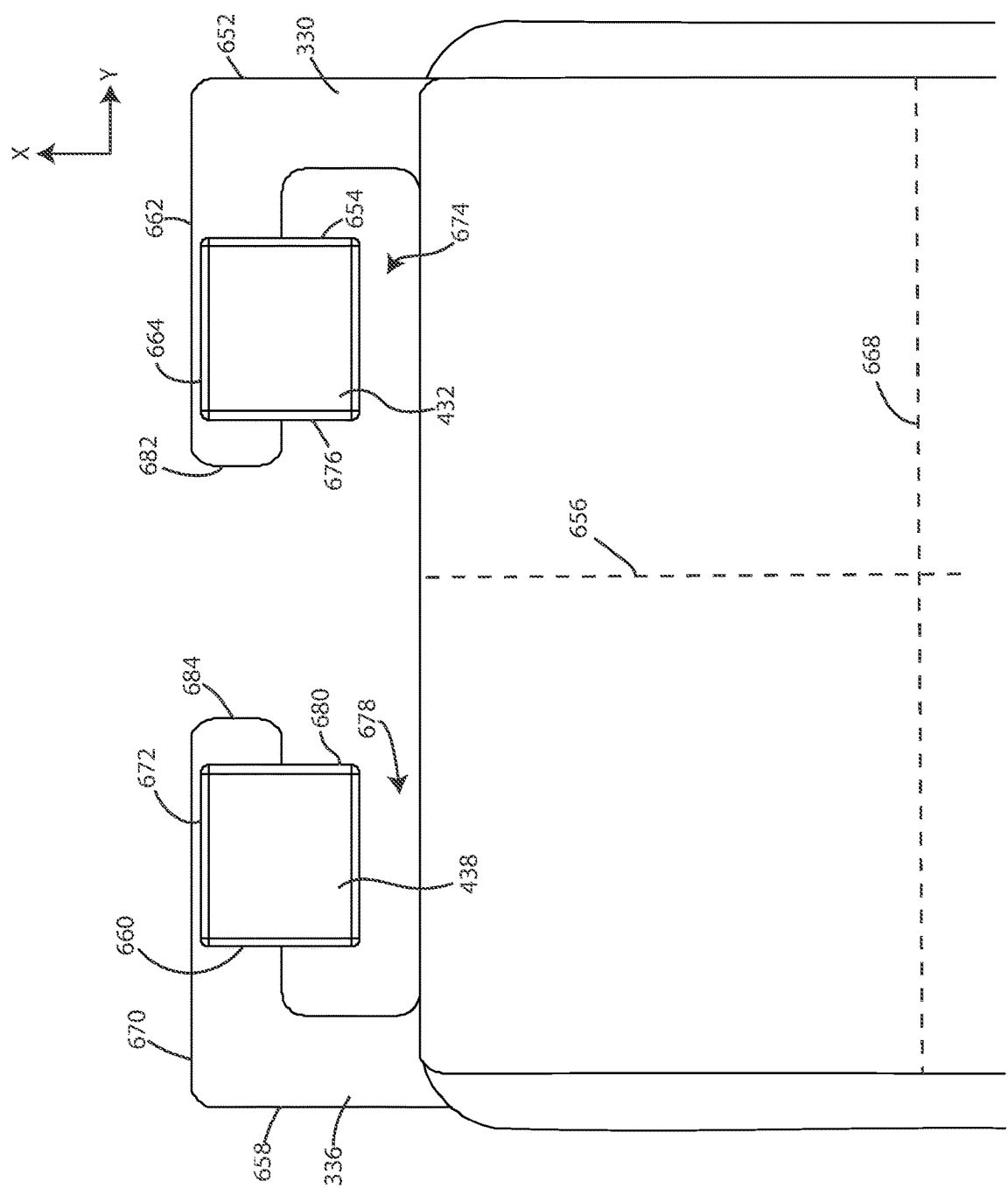
FIG. 6 is a top view of a portion of an electrochemical cell in accordance with various embodiments herein.
Figure 7:
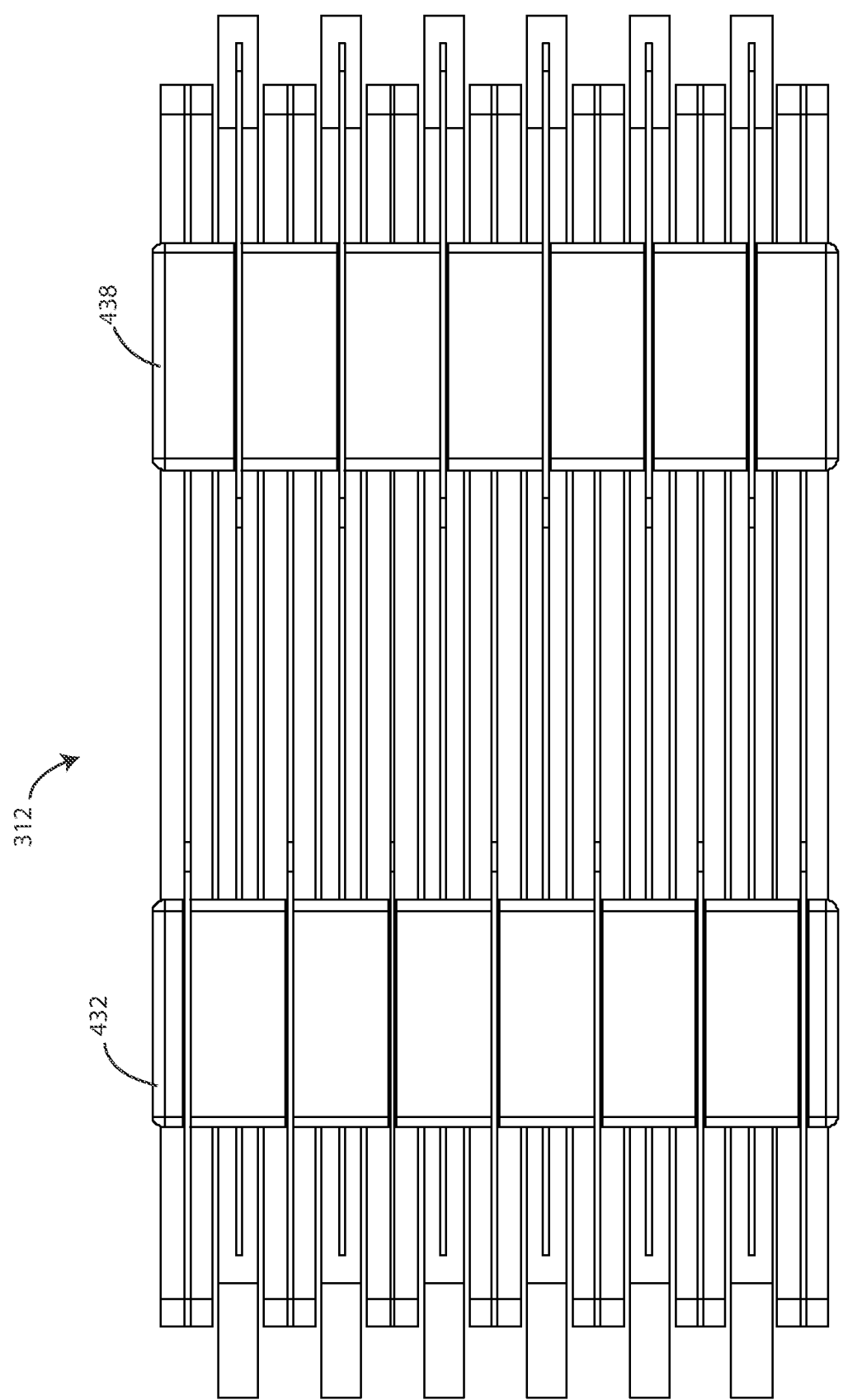
FIG. 7 is an end view of an electrochemical cell in accordance with various embodiments herein.

FIG. 4 shows a perspective view of an electrochemical cell 312 in accordance with various embodiments herein. FIG. 5 shows a top view of the electrochemical cell 312 and FIG. 6 shows a close-up top view of a portion of the electrochemical cell 312. FIG. 7 shows an end view of the electrochemical cell 312.

In some embodiments, the anode busbar 432 and the cathode busbar 438 can be substantially parallel with each other. In various embodiments, the anode busbar 432 and the cathode busbar 438 can be oriented substantially perpendicularly to a plane of the anode plates 320 and cathode plates 324.

In various embodiments, the anode busbar 432 can be oriented such that the anode tabs 330 are not disposed between the anode busbar 432 and the plurality of anode plates 320. Similarly, the cathode busbar 438 can be oriented such that the cathode tabs 336 are not disposed between the cathode busbar 438 and the plurality of cathode plates 324.

In various embodiments, the anode tabs 330 can extend further away from the stack of plates than the anode busbar 432 along the x-axis. The cathode tabs 336 can extend further away from the stack of plates than the cathode busbar 438 along the x-axis.

In some embodiments, at least a portion of the anode tabs 330 can extend further in each direction along the y-axis than the anode busbar 432, such as shown in FIGS. 5 and 6. At least a portion of the cathode tabs 336 can extend further in each direction along the y-axis than the cathode busbar 438.

In some embodiments, the anode tabs 330 can extend a distance 544 outward from an adjacent edge of the anode plates 320. The anode busbar 432 can be positioned such that the anode busbar 432 does not extend past a distance 546 from the adjacent edge of the anode plates 320. The distance 544 can be greater than the distance 546, such that the anode tabs 330 extend past the anode busbar 432.

Similarly, in some embodiments, the cathode tabs 336 can extend a distance 548 outward from an adjacent edge of the cathode plates 324. The cathode busbar 438 can be positioned such that the cathode busbar 438 does not extend past a distance 550 from the adjacent edge of the cathode plates 324. The distance 548 can be greater than the distance 550, such that the cathode tabs 336 extend past the cathode busbar 438.

The anode tabs 330 can include an outside edge 652, and the anode busbar 432 can include an outside edge 654, as shown in FIG. 6. The outside edge 652 of the anode tabs 330 can be further away from a centerline 656 of the anode plates 320 than the outside edge 654 of the anode busbar 432, such as when the centerline 656 extends along the x-axis or along the longitudinal axis of the electrochemical cell 312. Further, the cathode tabs 336 can include an outside edge 658, and the cathode busbar 438 can include an outside edge 660. The outside edge 658 of the cathode tabs 336 can be further away from the centerline 656 of the cathode plates 324 than the outside edge 660 of the cathode busbar 438.

The anode tabs 330 can include an outside edge 662, and the anode busbar 432 can include an outside edge 664. The outside edge 662 of the anode tabs 330 can be further away from a centerline 668 of the anode plates 320 than the outside edge 664 of the anode busbar 432, such as when the centerline 668 extends along the y-axis as shown in FIG. 6. Further, the cathode tabs 336 can include an outside edge 670, and the cathode busbar 438 can include an outside edge 672. The outside edge 670 of the cathode tabs 336 can be further away from the centerline 668 of the cathode plates 324 than the outside edge 672 of the cathode busbar 438.

The anode tabs 330 can include an inner edge 682, and the anode busbar 432 can include an inner edge 676. The inner edge 682 of the anode tabs 330 can be closer to the centerline 656 of the anode plates 320 than the inner edge 676 of the anode busbar 432. Further, the cathode tabs 336 can include an inner edge 684, and the cathode busbar 438 can include an inner edge 680. The inner edge 684 of the cathode tabs 336 can be closer to the centerline 656 of the cathode plates 324 than the inner edge 680 of the cathode busbar 438.

As previously mentioned, in some embodiments, the anode busbar 432 can be oriented such that the anode tabs 330 are not disposed between the anode busbar 432 and the plurality of anode plates 320, and the cathode busbar 438 can be oriented such that the cathode tabs 336 are not disposed between the cathode busbar 438 and the plurality of cathode plates 324. In some embodiments, a gap 674 can extend between the anode plates 320 and the anode busbar 432, such that the anode tab 330 does not extend between the anode busbar 432 and the anode plates 320 inside of the outside edge 654 and the inner edge 676. Similarly, a gap 678 can extend between the cathode plates 324 and the cathode busbar 438, such that the cathode tab 336 does not extend between the cathode busbar 438 and the cathode plates 324 inside of the outside edge 660 and the inner edge 680.

FIG. 7 shows an end view of the electrochemical cell 312 in accordance with various embodiments herein. In some embodiments, the anode busbar 432 can be parallel with the cathode busbar 438. In some embodiments, the anode busbar 432 and the cathode busbar 438 can be perpendicular to a plane of the anode plates 320 and cathode plates 324.

Figure 8:
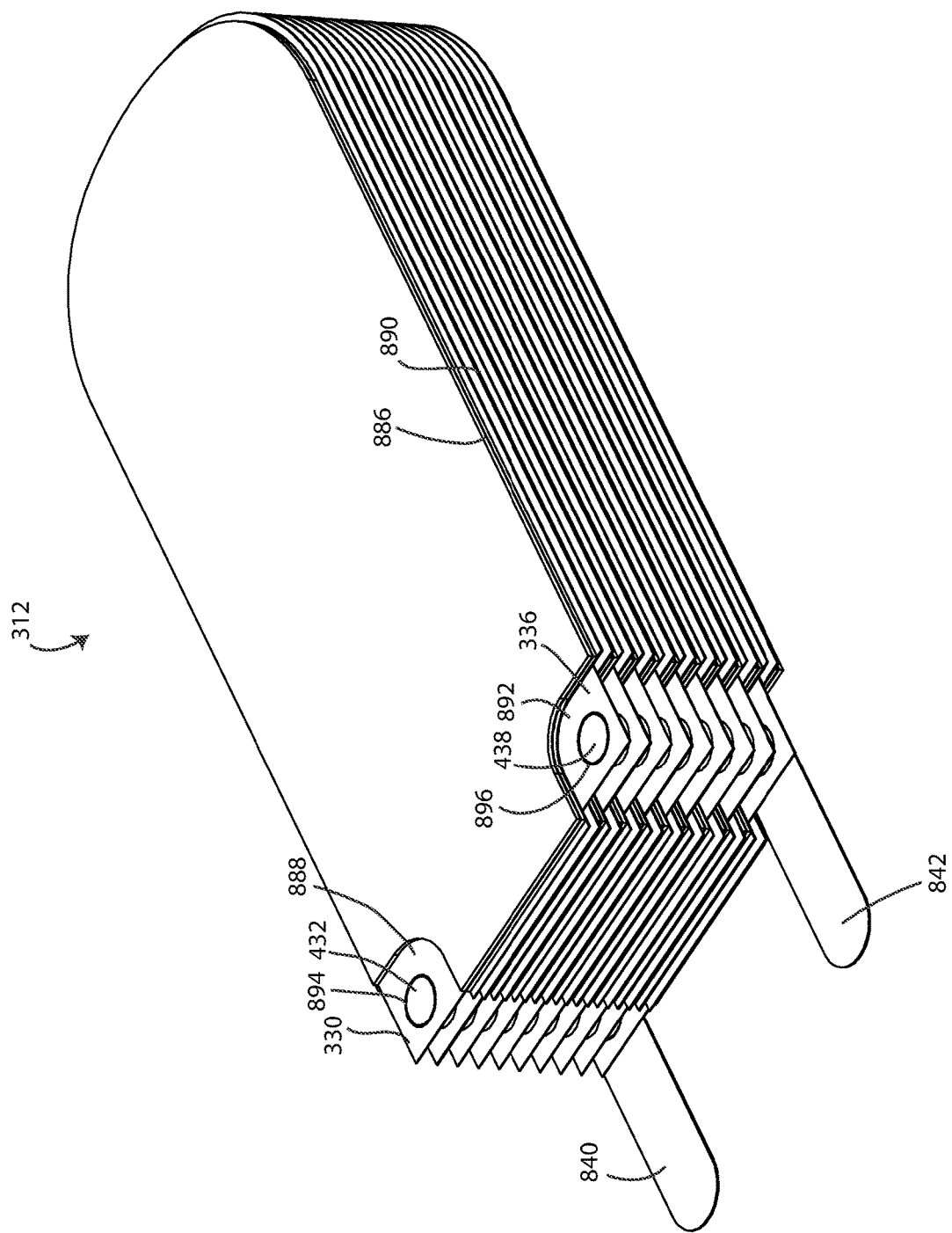
FIG. 8 is a perspective view of an electrochemical cell in accordance with various embodiments herein.
Figure 9:
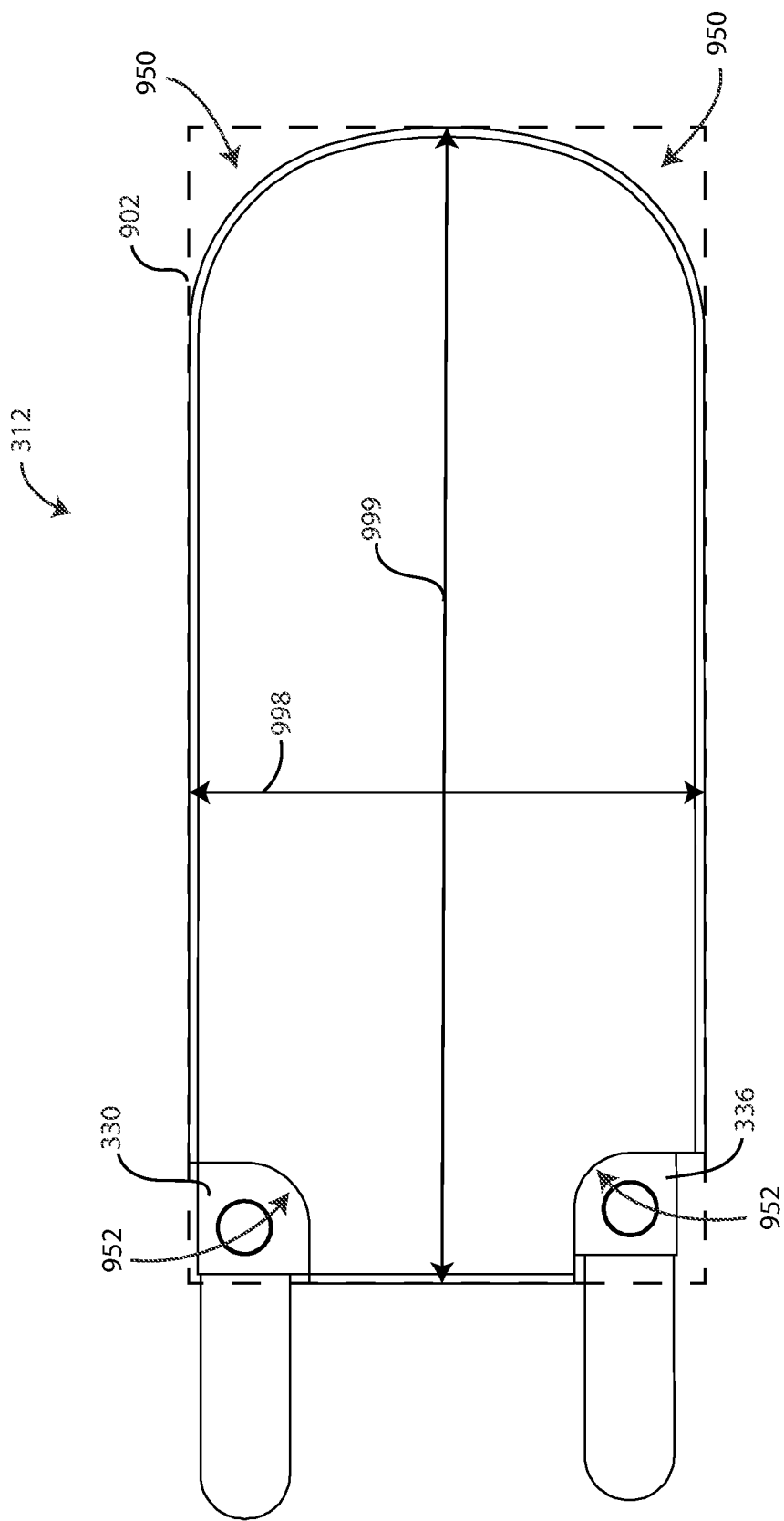
FIG. 9 is a top view of an electrochemical cell in accordance with various embodiments herein.
Figure 10:
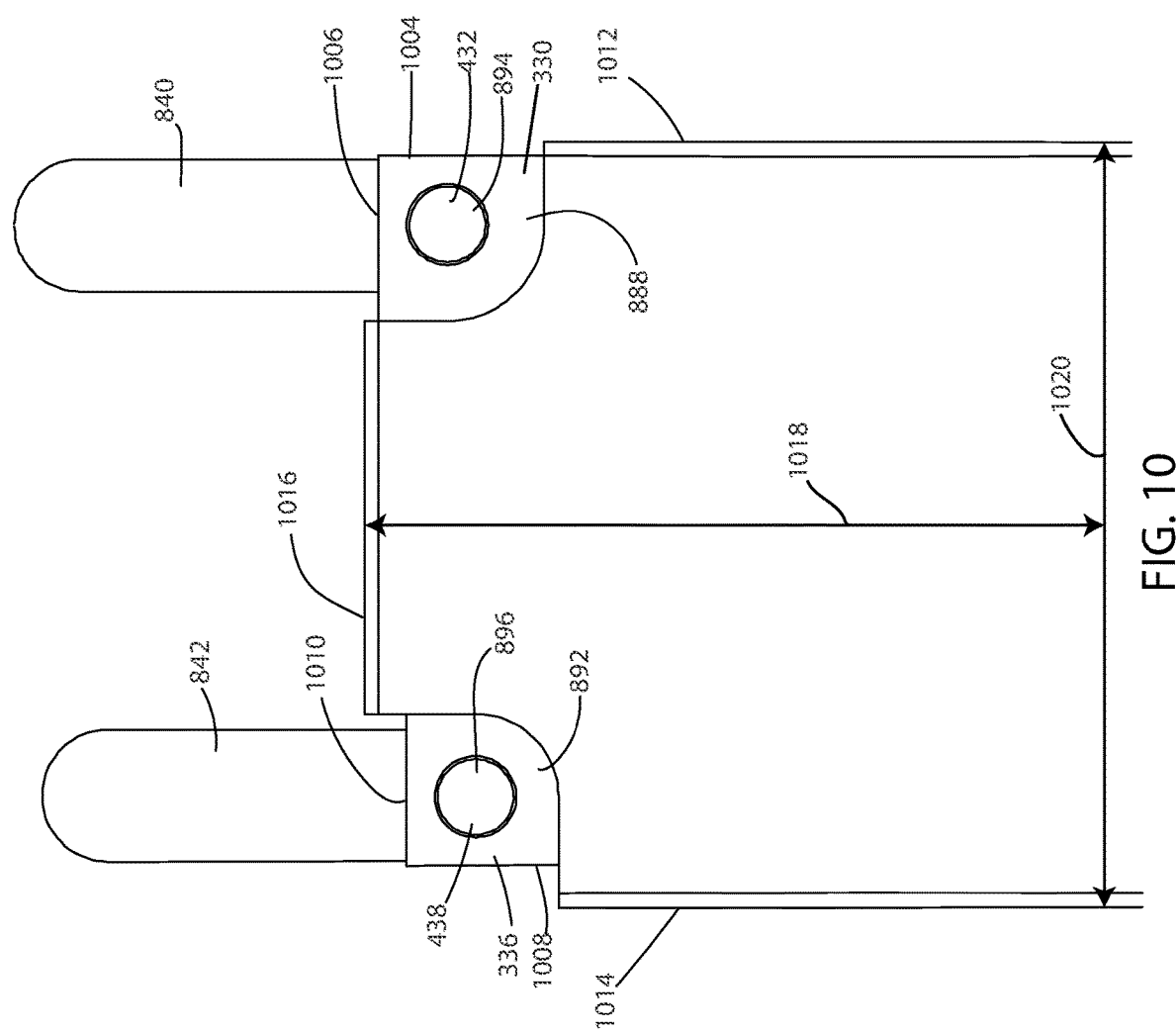
FIG. 10 is a top view of a portion of an electrochemical cell in accordance with various embodiments herein.
Figure 11:
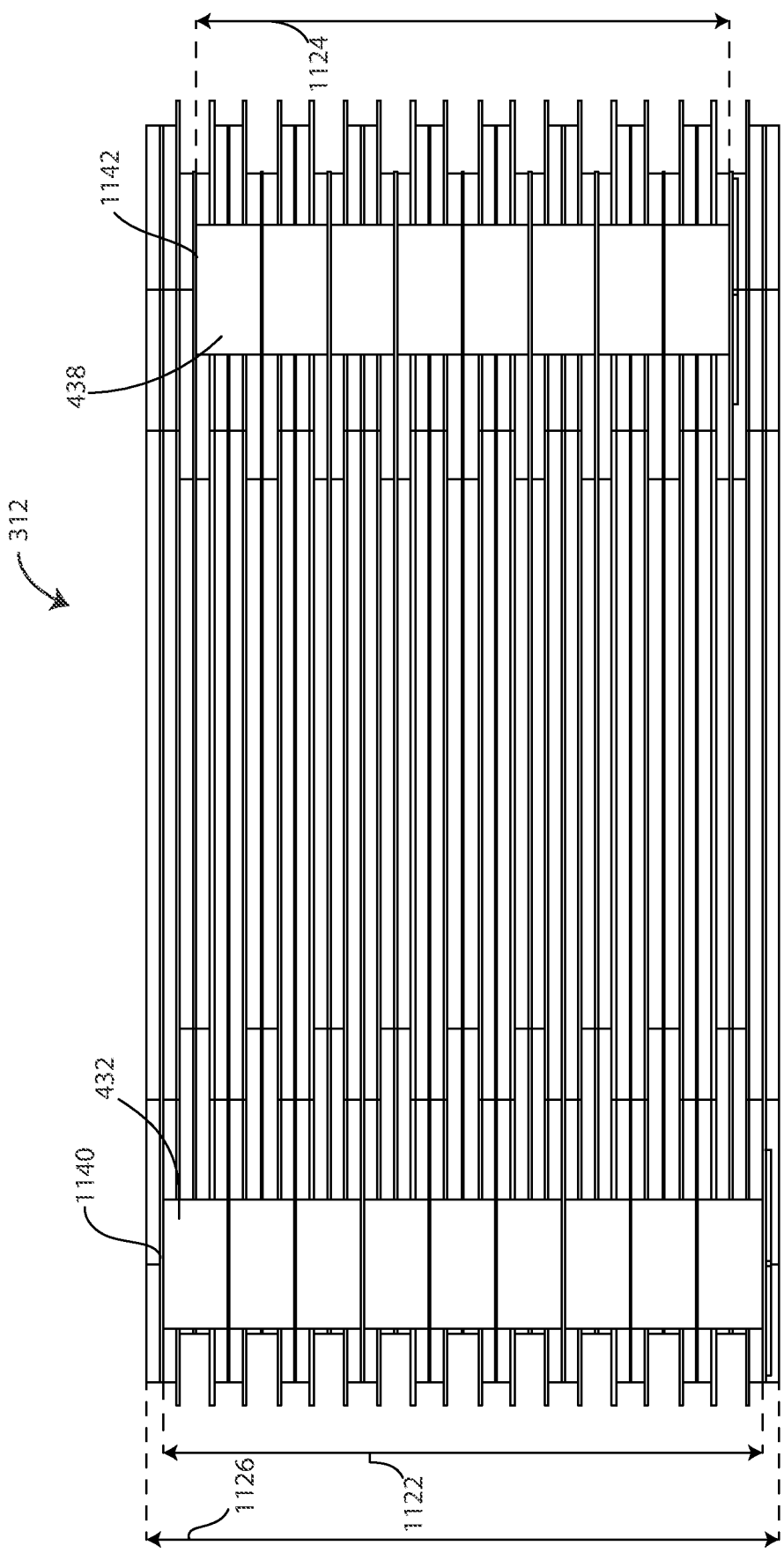
FIG. 11 is an end view of an electrochemical cell in accordance with various embodiments herein.

FIG. 8 shows a perspective view of an electrochemical cell 312 in accordance with various embodiments herein. FIG. 9 shows a top view of the electrochemical cell 312 shown in FIG. 8. FIG. 10 shows a close up of a portion FIG. 9. FIG. 11 shows an end view of the electrochemical cell 312 shown in FIG. 8.

In various embodiments, the outside peripheral surface 886 of the anode plates 320 defines a perimeter. The anode plates 320 define a void 888 which is located within the perimeter. The anode busbar 432 can be disposed within the perimeter, such as within the void 888. Similarly, in various embodiments, the outside peripheral surface 890 of the cathode plates 324 defines a perimeter. The cathode plates 324 define a void 892 which is located within the perimeter. The cathode busbar 438 can be disposed within the perimeter, such as within the void 892.

In various embodiments, the void 888 can be positioned adjacent to a corner of the anode plates 320, and the void 892 can be positioned adjacent to a corner of the cathode plates 324.

In some embodiments, the voids 888, 892 (or recesses, edge indentations, or edge cavities) can be greater than or equal to 1%, 2%, 3%, 4%, 5%, or 6.0% of the total surface area of the plates 320, 324. In some embodiments, the voids 888, 892 can be less than or equal to 15%, 14%, 13%, 12%, 11%, 10%, 9%, 8%, 7%, or 6.0% of the total surface area of the plates 320, 324. In some embodiments, the voids 888, 892 can fall within a range of 1% to 15.0%, or 2% to 14.0%, or 3% to 13.0%, or 4% to 12.0%, or 5% to 11.0%, or 6% to 10.0%, or can be about 5.0% or 10% of the total surface area of the plates 320, 324.

In some embodiments, the voids 888, 892 (or recesses, edge indentations, or edge cavities) can cover a surface area of greater than or equal to 0.1, 0.5, 1, 5, 9, 13, 17, 21, or 25 mm$^2$. In some embodiments, the surface area can be less than or equal to 100, 88, 75, 62, 50, 38, or 25 mm$^2$. In some embodiments, the surface area can fall within a range between any of the foregoing including, but not limited to, 0.1 to 100 mm$^2$, or 5 to 88 mm$^2$, or 9 to 75 mm$^2$, or 13 to 62 mm$^2$, or 17 to 50 mm$^2$, or 21 to 38 mm$^2$.

In various embodiments, the anode tabs 330 can be located within the void 888 and within the perimeter defined by the outside peripheral surface 886. In various embodiments, the cathode tabs 336 can be located within the void 892 and within the perimeter defined by the outside peripheral surface 890.

In some embodiments, the anode tabs 330 can define an aperture 894. The anode busbar 432 can be disposed within the aperture 894. In some embodiments, the aperture 894 is fully enclosed by the anode tabs 330 and in other embodiments the aperture 894 can be partially open. The anode busbar 432 can be connected to the anode terminal 842. The cathode tabs 336 can define an aperture 896. In some embodiments, the aperture 896 is fully enclosed by the cathode tabs 336 and in other embodiments the aperture 896 can be partially open. The cathode busbar 438 can be disposed within the aperture 896. The cathode busbar 438 can be connected to the cathode terminal 840.

In various embodiments, the anode plates 320 and cathode plates 324 can have a maximum width 998 and a maximum length 999. The maximum width 998 and maximum length 999 can define an outer boundary 902. In various embodiments, the voids 888, 892 can be located within the outer boundary 902. In various embodiments, the anode busbar 432 and the cathode busbar 438 can be located within the outer boundary 902. As shown in FIG. 9, two corners of the cathode and/or anode plates can include a convex curve 950 and two corners can include a concave curve 952.

The anode tabs 330 can include an outside edge 1004 (in the width direction), and the plates 320, 324 can have a first outside edge 1012 as shown in FIG. 10. The outside edge 1004 of the anode tabs 330 can be closer to, or an equal distance to, a centerline 1018 of the plates 320, 324 than the first outside edge 1012 of the plates 320, 324, such as when the centerline 1018 extends along the x-axis or along the longitudinal axis of the electrochemical cell 312. The cathode tabs 336 can include an outside edge 1008 (in the width direction), and the plates 320, 324 can have a second outside edge 1014 (opposite from the first outside edge 1012). The outside edge 1008 of the cathode tabs 336 can be closer to, or an equal distance to, a centerline 1018 of the plates 320, 324 than the second outside edge 1014 of the plates 320, 324.

The anode tabs 330 can include an outside edge 1006 (in the length direction), and the plates 320, 324 can have an outside edge 1016. The outside edge 1006 of the anode tabs 330 can be closer to, or an equal distance to, a centerline 1020 of the plates 320, 324 than the outside edge 1016 of the plates 320, 324, such as when the centerline 1020 extends along the y-axis of the electrochemical cell 312. The cathode tabs 336 can include an outside edge 1010. The outside edge 1010 of the cathode tabs 336 can be closer to, or an equal distance to, the centerline 1020 of the plates 320, 324 than the outside edge 1016 of the plates 320, 324.

The anode busbar 432 can be parallel with the cathode busbar 438 as shown in FIG. 11. The anode busbar 432 and the cathode busbar 438 can be perpendicular to a plane of the anode plates 320 and the cathode plates 324.

In various embodiments, the anode busbar 432 can have a height 1122. The cathode busbar 438 can have a height 1124. In some embodiments, the height 1122 of the anode busbar 432 can be equivalent to the height 1124 of the cathode busbar 438. In some embodiments, the height 1122 of the anode busbar 432 can be greater than the height 1124 of the cathode busbar 438. In some embodiments, the height 1122 of the anode busbar 432 can be less than the height 1124 of the cathode busbar 438.

In some embodiments, the height 1122 of the anode busbar 432 and/or the height 1124 of the cathode busbar 438 can be equivalent to the height 1126 of the plates 320, 324. In some embodiments, the height 1122 of the anode busbar 432 and/or the height 1124 of the cathode busbar 438 can be less than or greater than the height 1126 of the plates 320, 324.

In some embodiments, the top 1140 of the anode busbar 432 can be above the top 1142 of the cathode busbar 438, such that the anode busbar 432 can be offset from the cathode busbar 438 as shown in FIG. 11. In some embodiments, the top 1140 of the anode busbar 432 can be below the top 1142 of the cathode busbar 438. In some embodiments, the top 1140 of the anode busbar 432 can be aligned with the top 1142 of the cathode busbar 438.

FIG. 12 shows a top view of an electrochemical cell 312 in accordance with various embodiments herein. In some embodiments, the anode tab 330 and the cathode tab 336 can be located on opposite sides of both the centerline 1228 and the centerline 1230, such as shown in FIG. 12. In some embodiments, the anode tab 330 and the cathode tab 336 can be on opposite sides of the centerline 1228 and the same side of centerline 1230. In some embodiments, the anode tab 330 and the cathode tab 336 can be on opposite sides of the centerline 1230 and the same side of centerline 1228, such as shown in FIG. 9.

In some embodiments, the anode plates 320 and the cathode plates 324 can have substantially similar shapes. In some embodiments, the anode plates 320 and the cathode plates 324 can have a substantially rectangular shape, such as shown in FIG. 12. In some embodiments, the anode plates 320 and the cathode plates 324 can have partially rectangular shape with a rounded end, such as shown in FIGS. 5 and 9. In some embodiments, the anode plates 320 and the cathode plates 324 can have a substantially circular shape, such as shown in FIGS. 13 and 14.

FIG. 13 shows a top view of an electrochemical cell 312. In some embodiments, the anode tabs 330 and the cathode tabs 336 can extend in different directions. In some embodiments, the anode tabs 330 and the cathode tabs 336 extend in perpendicular directions, as shown in FIG. 13.

FIG. 14 shows a top view of an electrochemical cell 312. In some embodiments, the anode tabs 330 and the cathode tabs 336 can extend in a similar direction. In some embodiments, the anode tabs 330 and the cathode tabs 336 can extend parallel with each other, as shown in FIG. 14.

Welding

Components of devices herein and, specifically, batteries may be attached to one another through various processes including, but not limited to, soldering, welding, brazing, crimping, staking and the like. In particular embodiments, components of devices herein can specifically be attached to one another through a welding process. By way of example, busbars can be attached to tabs or other conductors through a welding process. Other components may also be attached to one another through welding.

Various welding techniques can be used. However, in many embodiments, a weld or weld line can be formed using a laser welding technique (or laser beam welding). The laser system can be a solid-state laser system or a gas laser system. Exemplary laser systems can include, but are not limited to, ruby lasers and Nd:YAG lasers, though other laser systems are also contemplated herein. Continuous or pulsed laser beam approaches can be used. In various embodiments herein, a pulsed laser beam approach can be used. In various embodiments, the pulses can be from one to several milliseconds.

Battery Chemistries

Batteries in accordance with embodiments herein can include both primary and secondary batteries. It will be appreciated that the space-efficient structures herein are not limited to any particular type of battery chemistry. However, in various embodiments herein, the electrochemical cell can be a primary lithium-manganese dioxide (Li anode/MnO2 cathode) battery. However, other primary and secondary battery chemistries are also contemplated herein. Other primary battery chemistries can include, but are not limited to, CFx, SVO, hybrid CFx/MnO$_2$, hybrid CFx/SVO, and the like.

In various embodiments, the battery includes a number of thin sheets of different materials that are sandwiched together to form a battery assembly. A repeating arrangement within the cell can include an anode assembly, a separator, and a cathode. The anode assembly can be formed from a sheet of material (such as a material including lithium) that constitutes an anode and a material that constitutes a current collector. A sheet of lithium material can be laminated to a substrate, such as a current collector. The current collector can be constructed from a number of different materials. For example, the current collector can be constructed from, among other alternatives, nickel or nickel-based material, stainless steel, aluminum, titanium, or copper, or any other suitable material. The current collector can include a uniform sheet, a wire grid, or other configurations. Further details of exemplary electrochemical cell components are described in U.S. Publ. Pat. Appl. Nos. 2008/0221629 and 2017/0317331, the content of which is herein incorporated by reference.

Various electrolyte compositions can be used with electrochemical cells or batteries herein. In some embodiments, the electrolyte can be non-aqueous (e.g., organic only electrolyte solvent). In some embodiments, the electrolyte is a 1M LiTFSi solution in ethylene carbonate, propylene carbonate and dimethoxy ethane. Various separators can be used with electrochemical cells or batteries herein.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. An electrochemical cell comprising:
    an anode comprising a plurality of anode plates each having outside peripheral surfaces;
    a cathode comprising a plurality of cathode plates each having outside peripheral surfaces, wherein the cathode plates are interposed between adjacent anode plates forming a stack of alternating anode and cathode plates;
    a separator positioned to provide physical separation between anode and cathode plates;
    a plurality of anode collectors in electrical communication with each anode plate;

a plurality of anode tabs in electrical communication with each anode collector;

a plurality of cathode collectors in electrical communication with each cathode plate;

a plurality of cathode tabs in electrical communication with each cathode collector; each cathode tab defining a tab surface that is parallel to the cathode plates;

an anode busbar interconnecting the plurality of anode tabs in parallel;

a cathode busbar interconnecting the plurality of cathode tabs in parallel;

the outside peripheral surfaces of the cathode plates defining a first perimeter;

the cathode plates defining a first void falling within the first perimeter, the first void positioned adjacent a corner of the cathode plates;

the cathode busbar disposed within the first perimeter;

the cathode tabs disposed within the first perimeter; and the cathode tabs defining an aperture in the first void into which the cathode busbar fits wherein the cathode tabs are substantially planar within the first perimeter; and wherein the first void does not contain spacers between the cathode tabs.

2. The electrochemical cell of claim 1, the outside peripheral surfaces of the anode plates defining a second perimeter; the anode plates defining a second void falling within the second perimeter; the anode busbar disposed within the second perimeter; and wherein the anode tabs are substantially planar within the second perimeter.

3. The electrochemical cell of claim 1, wherein the first void comprises less than 10 percent of the total surface area of the cathode plates.

4. The electrochemical cell of claim 2, the second void positioned adjacent a corner of the anode plates.

5. The electrochemical cell of claim 2, wherein the second void comprises less than 10 percent of the total surface area of the anode plates.

6. The electrochemical cell of claim 1, the anode tabs defining an aperture into which the anode busbar fits.

7. The electrochemical cell of claim 1, wherein the cathode plates and the anode plates are substantially rectangular.

8. The electrochemical cell of claim 7, wherein two corners of the substantially rectangular cathode plates and anode plates comprise a convex curve and two corners comprise a concave curve.

9. The electrochemical cell of claim 1, wherein the cathode plates and the anode plates are substantially circular.

10. The electrochemical cell of claim 1, wherein the first void covers a surface area of 0.1 $mm^2$ to 100 $mm^2$.

11. The electrochemical cell of claim 1, the cathode tabs comprising an outside edge, the cathode plates comprising an outside edge, wherein the outside edge of the cathode tabs is closer to a centerline of the cathode plates than the outside edge of the cathode plates.

12. The electrochemical cell of claim 1, wherein the height of the cathode busbar is substantially equal to the height of the stack of alternating anode and cathode plates.

13. The electrochemical cell of claim 1, wherein the first void covers a surface area of 0.1 $mm^2$ to 30 $mm^2$.

14. The electrochemical cell of claim 1, wherein the first void covers a surface area of 50 $mm^2$ to 100 $mm^2$.

15. An electrochemical cell comprising:
an anode comprising a plurality of anode plates each having outside peripheral surfaces;

a cathode comprising a plurality of cathode plates each having outside peripheral surfaces, wherein the cathode plates are interposed between adjacent anode plates forming a stack of alternating anode and cathode plates;

a separator positioned to provide physical separation between anode and cathode plates;

a plurality of anode collectors in electrical communication with each anode plate;

a plurality of anode tabs in electrical communication with each anode collector;

a plurality of cathode collectors in electrical communication with each cathode plate;

a plurality of cathode tabs in electrical communication with each cathode collector;

an anode busbar interconnecting the plurality of anode tabs in parallel;

a cathode busbar interconnecting the plurality of cathode tabs in parallel;

the outside peripheral surfaces of the cathode plates defining a first perimeter;

the cathode plates defining a first void falling within the first perimeter, the first void positioned adjacent a corner of the cathode plates;

the cathode busbar disposed within the first perimeter;

the cathode tabs disposed within the first perimeter; and the cathode tabs defining an aperture in the first void into which the cathode busbar fits wherein the cathode tabs are substantially planar within the first perimeter; and wherein the first void does not contain spacers between the cathode tabs.

* * * * *